US010555548B2

(12) United States Patent
Smith (10) Patent No.: US 10,555,548 B2
(45) Date of Patent: Feb. 11, 2020

(54) OZONE GENERATOR METHODS FOR RETROFIT OF ENCLOSED AND AIR-CONDITIONED ENVIRONMENTS

(71) Applicant: Quail Systems, LLC, Adamsville, TN (US)

(72) Inventor: Robert W. Smith, Adamsville, TN (US)

(73) Assignee: Quail Systems, LLC, Adamsville, TN (US)

( * ) Notice: Subject to any disclaimer, the term of this patent is extended or adjusted under 35 U.S.C. 154(b) by 0 days.

(21) Appl. No.: 16/426,742

(22) Filed: May 30, 2019

(65) Prior Publication Data

US 2019/0335790 A1 Nov. 7, 2019

Related U.S. Application Data

(62) Division of application No. 15/691,003, filed on Aug. 30, 2017, now Pat. No. 10,342,246.

(60) Provisional application No. 62/385,465, filed on Sep. 9, 2016.

(51) Int. Cl.
| | |
|---|---|
| *A61L 2/20* | (2006.01) |
| *A23L 3/3445* | (2006.01) |
| *C01B 13/11* | (2006.01) |
| *A23B 7/152* | (2006.01) |
| *A61L 2/26* | (2006.01) |

(52) U.S. Cl.
CPC ............ *A23L 3/3445* (2013.01); *A23B 7/152* (2013.01); *A61L 2/202* (2013.01); *A61L 2/26* (2013.01); *C01B 13/11* (2013.01); *C01B 13/115* (2013.01); *A23V 2002/00* (2013.01); *C01B 2201/12* (2013.01); *C01B 2201/90* (2013.01)

(58) Field of Classification Search
CPC .................................. A61L 2/202; A61L 9/015
See application file for complete search history.

(56) References Cited

U.S. PATENT DOCUMENTS

| | | | |
|---|---|---|---|
| 4,849,237 A | 7/1989 | Hurst | |
| 5,956,562 A * | 9/1999 | Lo | ............................ C01B 13/11 422/186.07 |
| 6,589,480 B1 | 7/2003 | Yuan | |

(Continued)

FOREIGN PATENT DOCUMENTS

| | | |
|---|---|---|
| CA | 2450117 | 12/2002 |
| CA | 2473540 | 7/2003 |

(Continued)

*Primary Examiner* — Donald R Spamer
(74) *Attorney, Agent, or Firm* — Pitts & Lake, P.C.; Jonathan M. Blanchard (57) ABSTRACT

An ozone generator includes at least four independent ozone generation control channels that energize at least four independent ozone generation plates. The at least four independent ozone generation control channels allow for multiple modes of operation, including sterilization, disinfecting, and managing, in addition to interleaved operation, which significantly extends the useful life of the individual ozone generation plates. The ozone generator is placed in a pre-existing conditioned airflow that enters a conditioned airspace enclosed by a container. Being placed in the preexisting conditioned airflow, the ozone generator does not require a fan or other air movement device to actively transport ozone-enriched air or oxygen through the ozone generator.

57 Claims, 6 Drawing Sheets

(56) References Cited

U.S. PATENT DOCUMENTS

| | | |
|---|---|---|
| 6,669,902 B1 | 12/2003 | Steiner |
| 6,893,610 B1 * | 5/2005 | Barnes .................. A61L 9/015 422/121 |
| 7,407,624 B2 | 8/2008 | Cumberland |
| 7,425,301 B2 | 9/2008 | Gillette |
| 7,614,260 B2 | 11/2009 | Daniels |
| 8,020,232 B2 | 9/2011 | Daniels |
| 8,056,358 B1 | 11/2011 | Shelton |
| 8,211,374 B2 | 7/2012 | Hallam |
| 8,226,899 B2 | 7/2012 | Woodbridge |
| 8,551,399 B2 | 10/2013 | Shannon |
| 8,636,951 B2 | 1/2014 | Shannon |
| 8,754,385 B1 | 6/2014 | Gutman |
| 8,984,914 B2 | 3/2015 | Daniels |
| 8,992,829 B2 | 3/2015 | Shannon |
| 9,034,251 B1 | 5/2015 | Gutman |
| 9,375,500 B2 | 6/2016 | Dunkley |
| 9,616,144 B2 | 4/2017 | Shannon |
| 9,657,423 B2 | 5/2017 | Daniels |
| 2003/0039729 A1 | 2/2003 | Murphy |
| 2003/0071069 A1 | 4/2003 | Shelton |
| 2003/0156978 A1 | 8/2003 | Gillette |
| 2004/0003511 A1 | 1/2004 | Silver |
| 2005/0011372 A1 | 1/2005 | Corrigan |
| 2005/0129571 A1 | 6/2005 | Centanni |
| 2006/0104858 A1 | 5/2006 | Potember |
| 2006/0273186 A1 | 12/2006 | Corrigan |
| 2007/0086914 A1 | 4/2007 | Antinozzi |
| 2007/0217987 A1 | 9/2007 | Belanger |
| 2008/0031770 A1 | 2/2008 | Heselton |
| 2008/0092745 A1 | 4/2008 | Tsao |
| 2008/0159910 A1 * | 7/2008 | Dick ...................... A23B 7/152 422/40 |
| 2008/0213125 A1 | 9/2008 | Boast |
| 2008/0227680 A1 | 9/2008 | Lynn |
| 2009/0120473 A1 | 5/2009 | Lynn |
| 2009/0233839 A1 | 9/2009 | Lynn |
| 2010/0107343 A1 | 5/2010 | Daniels |
| 2012/0020832 A1 | 1/2012 | Onge |
| 2012/0063949 A1 | 3/2012 | Jennings |
| 2012/0100037 A1 | 4/2012 | Shannon |
| 2012/0142575 A1 | 6/2012 | Lynn |
| 2014/0033445 A1 | 2/2014 | Daniels |
| 2014/0037499 A1 | 2/2014 | Shannon |
| 2014/0302168 A1 | 10/2014 | Perry |
| 2015/0329225 A1 | 11/2015 | Moncayo, Jr. |
| 2015/0343336 A1 | 12/2015 | Mackay Pett |

FOREIGN PATENT DOCUMENTS

| | | |
|---|---|---|
| CA | 2486831 | 2/2004 |
| CA | 2491781 | 7/2005 |
| CA | 2602230 | 9/2005 |
| CA | 2526367 | 4/2007 |
| CA | 2534700 | 7/2007 |
| CA | 2641046 | 8/2007 |
| CA | 2450117 | 4/2011 |
| CN | 1537638 | 10/2004 |
| CN | 102908639 | 2/2013 |
| CN | 202738766 | 2/2013 |
| CN | 104233706 | 12/2014 |
| CN | 205045923 | 2/2016 |
| EP | 1968653 | 2/2013 |
| EP | 1973578 | 4/2013 |
| GB | 2468519 | 9/2010 |
| GB | 2468519 | 1/2014 |
| GB | 2468520 | 1/2014 |
| KR | 200200575 | 8/2000 |
| KR | 101291844 | 7/2013 |
| WO | WO9938374 | 8/1999 |
| WO | WO2004011041 | 2/2004 |
| WO | WO2005060385 | 7/2005 |
| WO | WO2005087278 | 9/2005 |
| WO | WO2009046562 | 4/2009 |
| WO | WO2011085466 | 7/2011 |
| WO | WO2012037678 | 3/2012 |
| WO | WO2013112197 | 8/2013 |
| WO | WO2016157383 | 10/2016 |

* cited by examiner

OZONE GENERATOR METHODS FOR RETROFIT OF ENCLOSED AND AIR-CONDITIONED ENVIRONMENTS

REFERENCE TO RELATED APPLICATIONS

This application is a division of U.S. Nonprovisional application Ser. No. 15/691,003, filed Aug. 30, 2017, entitled "Ozone Generator, System, and Methods for Retrofit of Enclosed and Air-Conditioned Environments," which claims the benefit of U.S. Provisional Application No. 62/385,465 entitled "Ozone Generator, System, and Methods for Retrofit of Enclosed and Air-Conditioned Environments" filed Sep. 9, 2016, both of which are incorporated by reference in the entirety.

BACKGROUND

Refrigerated containers are commonly used for shipping perishable cargo, such as fresh produce and other foods, which must be maintained during transit at a temperature within a specified temperature range, thus temperature controlled, to maintain freshness and minimize spoilage. By separating the atmosphere outside the container from the atmosphere inside the container, an enclosed airspace that may be temperature controlled, and thus conditioned, is created. In addition to temperature, the relative humidity, oxygen content, and other parameters may be controlled in the enclosed airspace. Refrigerated containers of this type may be designed to accommodate transport by road on trailers, by sea on container ships, by rail on flat-bed train cars, and by air in cargo planes. While the container may be detachable from the transport vehicle, the container may be fixed to a truck chassis or to a semi-trailer chassis when the transport vehicle is dedicated to transporting refrigerated fresh produce and food. Such dedicated produce and other food transport vehicles are often referred to as reefer trucks.

Refrigerated containers are equipped with a refrigeration unit, commonly referred to as a reefer, which is secured to one wall of the container or to the transport vehicle. The refrigeration unit includes a compressor, a compressor motor, a condenser unit isolated from the enclosed airspace, and an evaporator unit in airflow communication with the interior of the enclosed airspace. In this way, the refrigeration unit can transfer heat from the conditioned airspace enclosed by the container to the atmosphere surrounding the exterior of the container. The refrigeration unit receives electrical power from an external source, such as the transport vehicle or a dedicated generator integrated with the container.

Produce and other foods spoil due to microorganism growth and the generation of spoilage gases, such as ethylene, which increase the rate of spoilage. While light and dehydration also can cause spoilage, when the produce and other foods are transported in an enclosed airspace, microorganism growth and spoilage gases are the primary factors. Microorganisms may include bacteria, viruses, fungus, and mold.

Although not commonly considered, food is refrigerated to substantially slow, not to substantially eliminate, microorganism growth. While slowing microorganism growth through refrigeration is effective, it would be preferable to kill the microorganisms as opposed to only slowing their growth. Thus, refrigeration may be supplemented with sterilants that focus on killing as opposed to slowing the growth of the undesirable microorganisms.

While chemical sterilants have been used to prolong the storage life of produce and other foods, chemical sterilants create the problem of having to remove the sterilant before the produce or other foods are eaten. Many types of food cannot be cleaned of the chemical sterilant before consumption, thus preventing the use of chemical sterilants for these food types.

One way to prolong the storage life of produce and other foods without using chemical sterilants is through the use of ozone, an allotrope of oxygen. Ozone has the ability to directly oxidize harmful bacteria, mold, and spoilage gasses, such as ethylene, thus rendering the bacteria, mold, and spoilage gasses inert from a produce and other food spoilage perspective. Generally, ozone concentrations of 0.1 ppm in an enclosed airspace will destroy microorganisms and eliminate most odors within 48 hours. Although conventional systems have attempted to use ozone as an effective sterilant for produce and other foods, there have been multiple disadvantages.

One disadvantage of conventional produce and other food ozone sterilization systems has been a difficulty in successfully retrofitting existing refrigerated containers with the ozone sterilization system, often arising from the variability in enclosed airspace volumes and the variability in produce and other food types being transported. Another disadvantage has been the inability of these conventional systems to provide enough ozone to effectively control microorganism growth due to an inability to generate and maintain the needed levels of ozone within the container before the container is loaded with produce or other foods before and during transport. Another disadvantage of conventional produce and other food ozone sterilization systems is their relatively high failure rate in actual use.

As seen from the above description, there is an ongoing need for improved devices and methods for at least partially sterilizing produce and other foods before and during transport to extend post-transport shelf life and freshness. The devices, methods, and systems of the present invention overcome at least one of the disadvantages associated with conventional refrigeration-only or refrigeration plus ozone produce and other food transport devices and methods.

SUMMARY

In one aspect, the invention provides a conditioned airflow ozone generator.

In another aspect of the invention, there is a method of positioning a conditioned airflow ozone generator in a previously existing conditioned airflow.

In another aspect of the invention, there is a method of operating a conditioned airflow ozone generator in an enclosed airspace in a previously existing conditioned airflow to extend produce and other foods shelf-life after shipment.

In another aspect of the invention, there is a conditioned airflow ozone generator system for an enclosed airspace.

Other systems, methods, features and advantages of the invention will be, or will become, apparent to one with skill in the art upon examination of the following figures and detailed description. It is intended that all such additional systems, methods, features, and advantages be included within this description, be within the scope of the invention, and be protected by the claims that follow. Thus, The scope of the present invention is defined solely by the appended claims and is not affected by the statements within this summary.

BRIEF DESCRIPTION OF THE DRAWINGS

The invention can be better understood with reference to the following drawings and description. The components in the figures are not necessarily to scale, emphasis instead being placed upon illustrating the principles of the invention.

FIG. 1A-1 represents an example of vehicles that may be used to transport produce and other foods in a refrigerated container.

FIG. 1A-2 represents another example of vehicles that may be used to transport produce and other foods in a refrigerated container.

DETAILED DESCRIPTION

An ozone generator includes at least four independent ozone generation control channels that energize at least four independent ozone generation plates. The at least four independent ozone generation control channels allow for multiple modes of operation, including sterilization, disinfecting, and managing, in addition to interleaved plate operation, which significantly extends the useful life of the individual ozone generation plates. The ozone generator is placed in a preexisting conditioned airflow that enters a conditioned airspace enclosed by a container. Being placed in the preexisting conditioned airflow, the ozone generator does not require a fan or other air movement device to actively transport ozone-enriched air or oxygen through the ozone generator.

The ozone generator preferably does not generate ozone in a separate enclosure and then introduce the ozone-enriched air or oxygen to the enclosed airspace, but directly generates ozone in the enclosed airspace where produce and other foods are stored for transport. Neither is an active ozone decomposer, such as an appropriate wavelength ultraviolet (UV) light, used to reduce generated ozone levels within the enclosed airspace. Instead, the ozone levels are monitored in the conditioned airspace and/or preexisting conditioned airflow so appropriate levels are maintained. The ozone generator also may be turned off at a pre-selected time period to provide decomposition of the ozone within the conditioned airspace before the conditioned airspace is entered by a person.

Figure 1A:
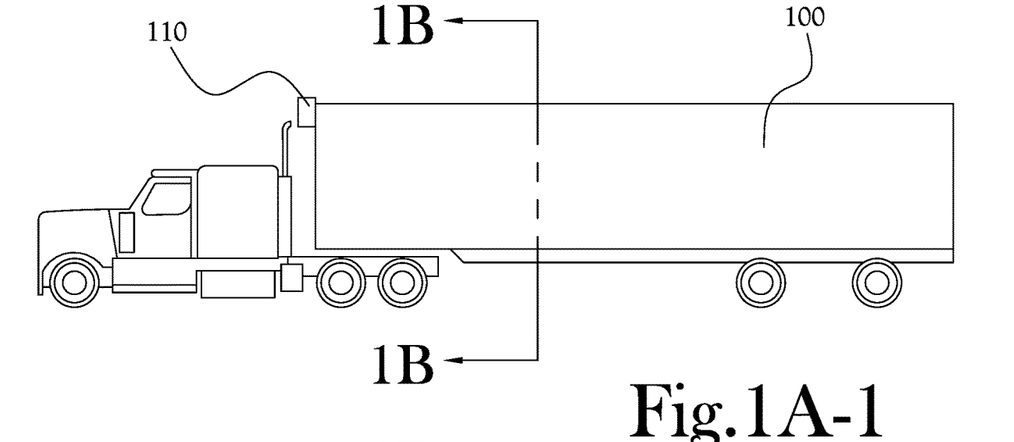
Figure 1A:
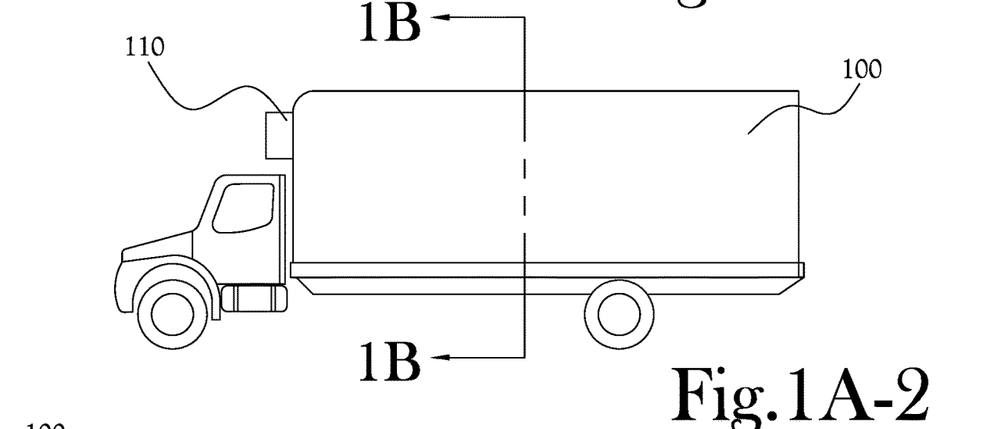

FIG. 1A-1 and FIG. 1A-2 represent two examples of vehicles that may be used to transport produce and other foods in a refrigerated container 100. Other types of vehicles may be used to transport the refrigerated container 100.

Figure 1B:
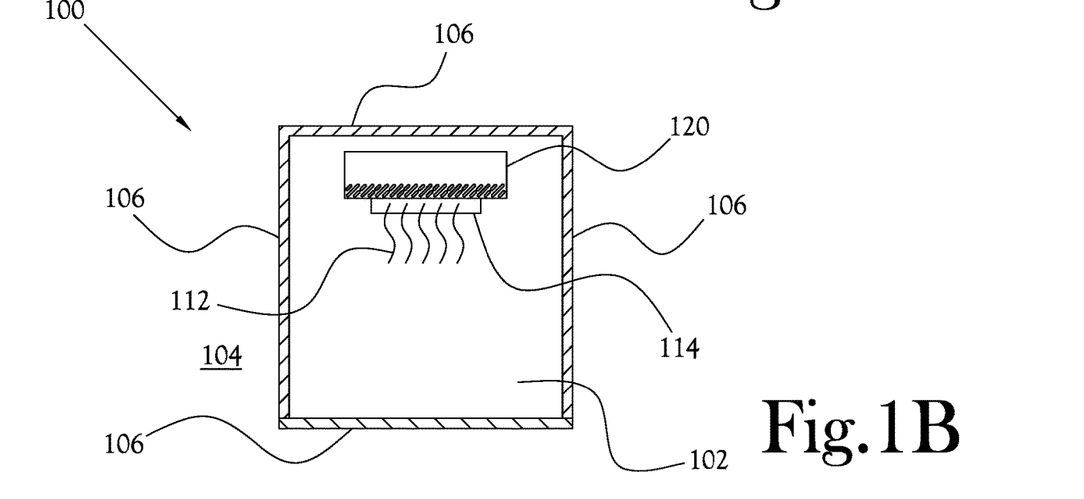
FIG. 1B represents the refrigerated container enclosing a conditioned airspace.

FIG. 1B represents the refrigerated container 100 enclosing a conditioned airspace 102. The refrigerated container 100 substantially separates the interior conditioned airspace 102 from an exterior airspace 104 substantially excluded by walls 106 of the refrigerated container 100. A refrigeration unit 110 is operatively associated with the refrigerated container 100 and provides conditioned airflow 112 to the conditioned airspace 102 through inlet duct 114. An outlet duct (not shown) transfers post-conditioned airflow back to the refrigeration unit 110 to be conditioned. Ozone generator 120 is positioned in the conditioned airflow 112 to provide ozone to the conditioned airflow 112. As the ozone generator 120 is position in the preexisting conditioned airflow, the ozone generator 120 does not require motors, fans, pumps, or the like to generate airflow through the ozone generator 120. Thus, a portion of the conditioned airflow 112 from the inlet duct 114 passes through the ozone generator 120, while another portion of the conditioned airflow 112 does not. Preferably, the ozone generator 120 is placed to cover no more than 50% of the area of the inlet duct 114 exposed to the interior conditioned airspace 102. Preferably, the portion of the ozone generator 120 including perforations 160 is placed to cover the inlet duct 114, while non-perforated portion 180 does not cover the inlet duct 114. Preferably, the ozone generator 120 is positioned from 8 to 20 centimeters (cm) away from the inlet duct 114. More preferably, the ozone generator 120 is positioned from 12 to 18 centimeters (cm) away from the inlet duct 114. The refrigerated container too may be loaded with fresh produce and other foods for transport. The refrigerated container too may include additional components.

Figure 2A:
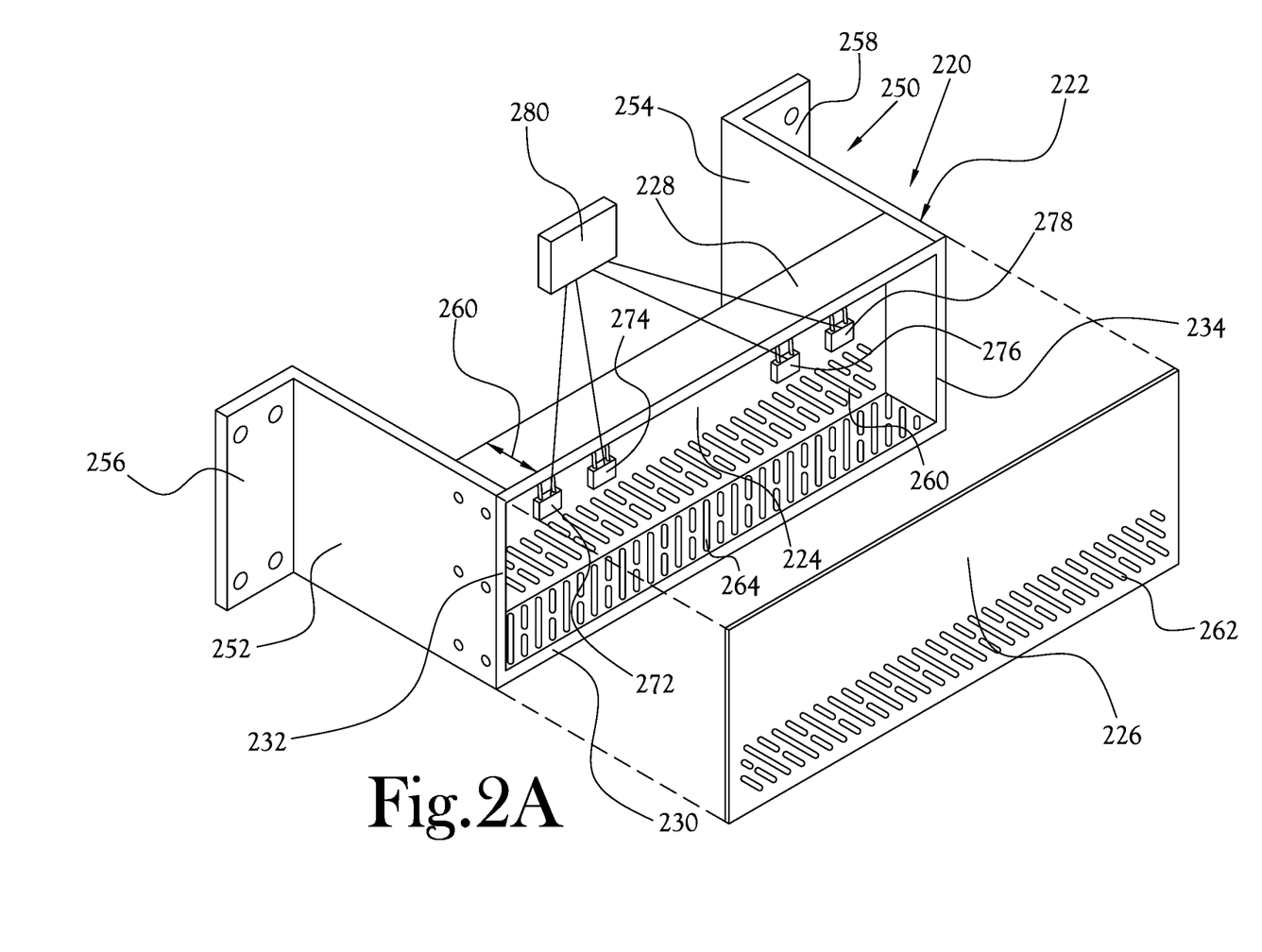
FIG. 2A represents an cross-section of an ozone generator including an enclosure including a back attached to a front through a top, a bottom, a left side, and a right side.

FIG. 2A represents an cross-section of an ozone generator 220 including an enclosure 222 including a back 224 attached to a front 226 through a top 228, a bottom 230, a left side 232, and a right side 234. The parts of the enclosure 222 may be individual pieces or formed together, such as when the back 224, the top 228, the bottom 230, and the left and the right sides 232, 234 are formed as a single part, but the front 226 is distinct and removable. The enclosure 222 includes at least four ozone generation plates 272, 274, 276, 278. The ozone generator 220 also includes attachments 250 that position the ozone generator 220 in a previously existing conditioned airflow.

The back 224 of the enclosure 222 includes perforations 260 through the material forming the back 224 that penetrate from 10% to 70% (surface area/surface area) of the surface area of the back 224. Preferably, the perforations 260 are present through from 20% to 35% of the surface area of the material forming the back 224. Preferably, the perforations 260 are located in the lower portion of the material forming the back 224, allowing for solid material above the perforations 260. Preferably, the perforations 260 are not located in at least the upper 30% of the material forming the back 224. While slot-type perforations of different lengths are depicted, other sizes, shapes, and orientations of perforation may be used to allow airflow through the material forming the back 224. While the back 224 is represented as being rectangular, such as approximately 20 cm. by approximately 70 cm., other shapes, such as a square, and other dimensions, may be used. The material forming the back 224 may be metal, plastic, ceramic, composite, and the like. Preferably, the material forming the back is metal or plastic, and more preferably, metal having a non-conductive coating.

The front 226 of the enclosure 222 includes perforations 262 through the material forming the front 226 that penetrate from 10% to 70% (surface area/surface area) of the surface area of the front 226. Preferably, the perforations 262 are present through from 20% to 35% of the surface area of the material forming the front 226. Preferably, the perforations 262 are located in the lower portion of the material forming the front 226, allowing for solid material above the perforations 262. Preferably, the perforations 262 are not located in at least the upper 30% of the material forming the front 226. While slot-type perforations of different lengths are depicted, other sizes, shapes, and orientations of perforation may be used to allow airflow through the material forming the front 226. While the front 226 is represented as being rectangular, such as approximately 20 cm. by approximately 70 cm., other shapes, such as a square, and other dimensions, may be used in accord with the shape and dimensions of the back 224. The material forming the front 226 may be metal, plastic, ceramic, composite, and the like. Preferably, the material is metal or plastic, and more preferably, metal having a non-conductive coating.

The top 228 of the enclosure 222 preferably lacks perforations through the material forming the top 228. While the top 228 is represented as being rectangular, such as approximately 7 cm. by approximately 70 cm., other shapes, such as a square, and other dimensions, may be used in accord with the shape and dimensions of the back 224 and the front 226. The material forming the top 228 may be metal, plastic, ceramic, composite, and the like. Preferably, the material is metal or plastic, and more preferably, metal having a non-conductive coating.

Figure 2B:
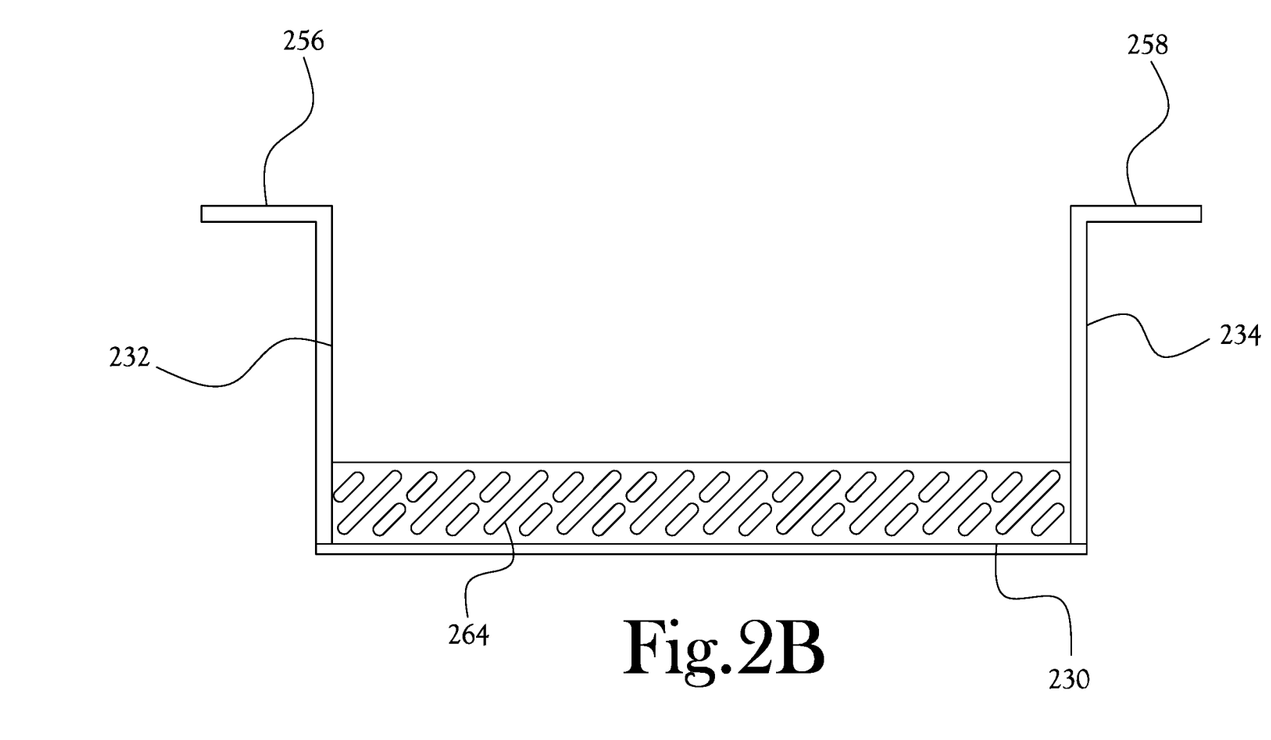
FIG. 2B is a representation of the bottom, where the perforations are shown.

The bottom 230 of the enclosure 222 includes perforations 264 through the material forming the bottom 230 that penetrate from 30% to 95% (surface area/surface area) of the surface area of the bottom 230. Preferably, the perforations 264 are present through from 60% to 80% of the surface area of the material forming the bottom 230. Preferably, the perforations 264 are located throughout the material forming the bottom 230, allowing for the substantially even distribution of solid material throughout the bottom 230. While slot-type perforations of different lengths are depicted, other sizes, shapes, and orientations of perforation may be used to allow airflow through the material forming the bottom 230. While the bottom 230 is represented as being rectangular, such as approximately 7 cm. by approximately 70 cm., other shapes, such as a square, and other dimensions, may be used in accord with the shape and dimensions of the back 224, the front 226, and the top 228. The material forming the bottom 230 may be metal, plastic, ceramic, composite, and the like. Preferably, the material is metal or plastic, and more preferably, metal having a non-conductive coating. FIG. 2B is another representation of the bottom 230, where the perforations 264 are shown.

The left side 232 and the right side 234 of the enclosure 222 are depicted as solid material, but could have perforations in their lower portions, for example. While the left side 232 and the right side 234 are represented as being rectangular, such as approximately 7 cm. by approximately 18 cm., other shapes, such as a square, and other dimensions, may be used in accord with the shape and dimensions of the back 224, the front 226, the top 228, and the bottom 230. The material forming the left side 232 and the right side 234 may be metal, plastic, ceramic, composite, and the like. Preferably, the material is metal or plastic, and more preferably, metal having a non-conductive coating.

Figure 2C:
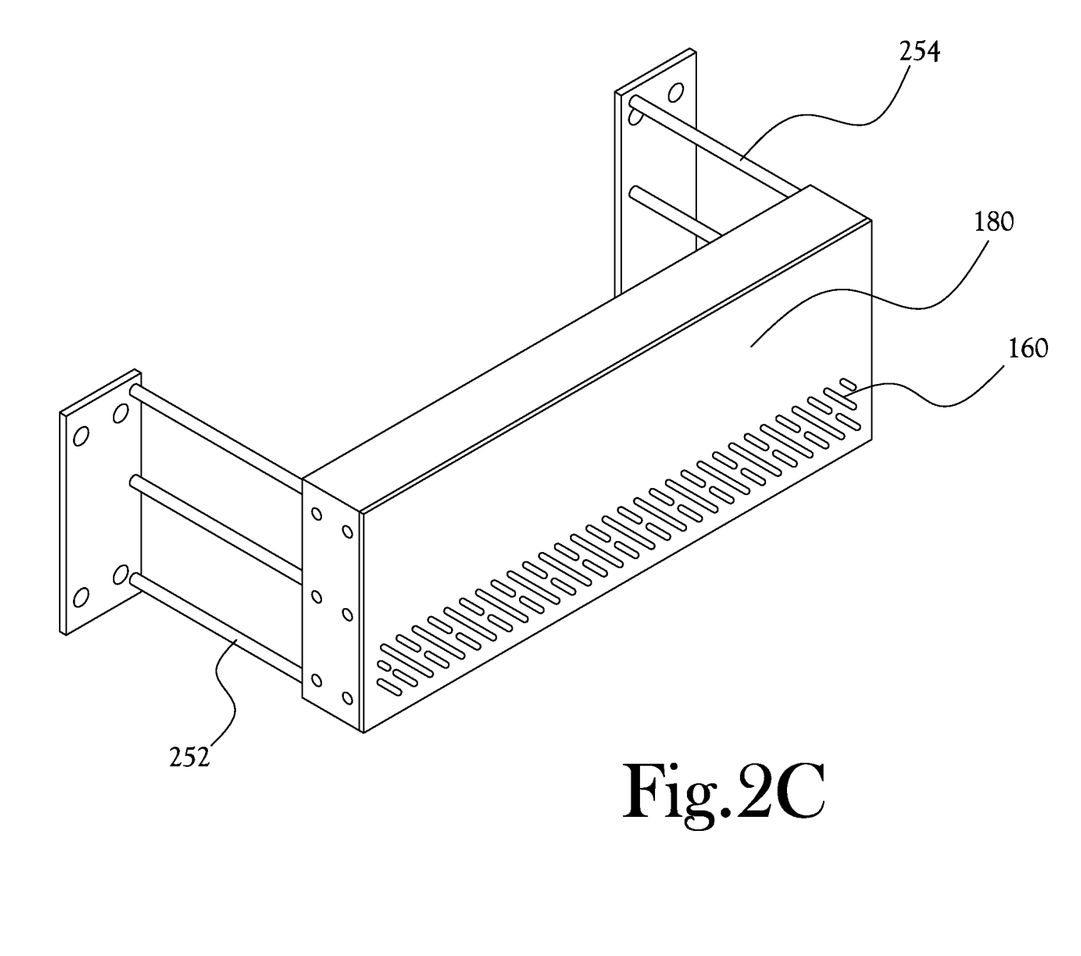
FIG. 2C represents the attachment sides as multiple rods, for example.

The attachments 250 of the ozone generator 220 include a left attachment side 252 and a right attachment side 254 that extend from the enclosure 222 to a left attachment member 256 and a right attachment member 258, respectively. The attachment sides 252, 254 extend at least 40% (length/length) of a width 260 of the enclosure sides 232, 234 between the back 224 and the front 226. While the attachment sides 252, 254 are represented as being rectangular, other shapes, such as a square may be used in accord with the shape of the back 224, the front 226, the top 228, and the bottom 230. While the attachment sides 252, 254 are represented as being solid plates, they may be a single rod or bar, multiple rods, bars, or plates, or other structures that can maintain attachment between the enclosure 222 and the attachment members 256, 258 during use of the ozone generator 220. FIG. 2C represents the attachment sides 252, 254 as multiple rods, for example. Although FIG. 2A represents the attachment sides 252, 254 as being integral with the left and the right sides 232, 234, respectively, the attachment sides 252, 254 may be distinct from the left and the right sides 232, 234. The material forming the attachment sides 252, 254 may be metal, plastic, ceramic, composite, and the like. Preferably, the material is metal, and more preferably, metal having a non-conductive coating.

The attachment members 256, 258 provide the surface that is attached to the interior of the container too as represented in FIG. 1B. While rectangular plates having holes for bolts, rivets, or the like may be used for attachment, other shapes may be used. The attachment members 256, 258 may lack holes if the ozone generator 220 is welded to the interior of the container too, for example.

The at least four ozone generation plates 272, 274, 276, 278 are independently operable through plate energizer 280. While a single plate energizer 280 is shown, a separate energizer for each plate could be used and the like. By independently operable it is meant that any one or more of the at least four ozone generation plates 272, 274, 276, 278 may be turned on or off respective of the other plates. Thus, if the desired ozone output from the ozone generator is not achieved with the ozone generation plate 272, the ozone generation plate 274, 276, and/or 278 may be energized. Similarly, two, three, or all four of the plates may be energized to further increase ozone output from the ozone generator 220. Thus, there are four independent ozone generation control channels within the plate energizer 380.

Figure 3:
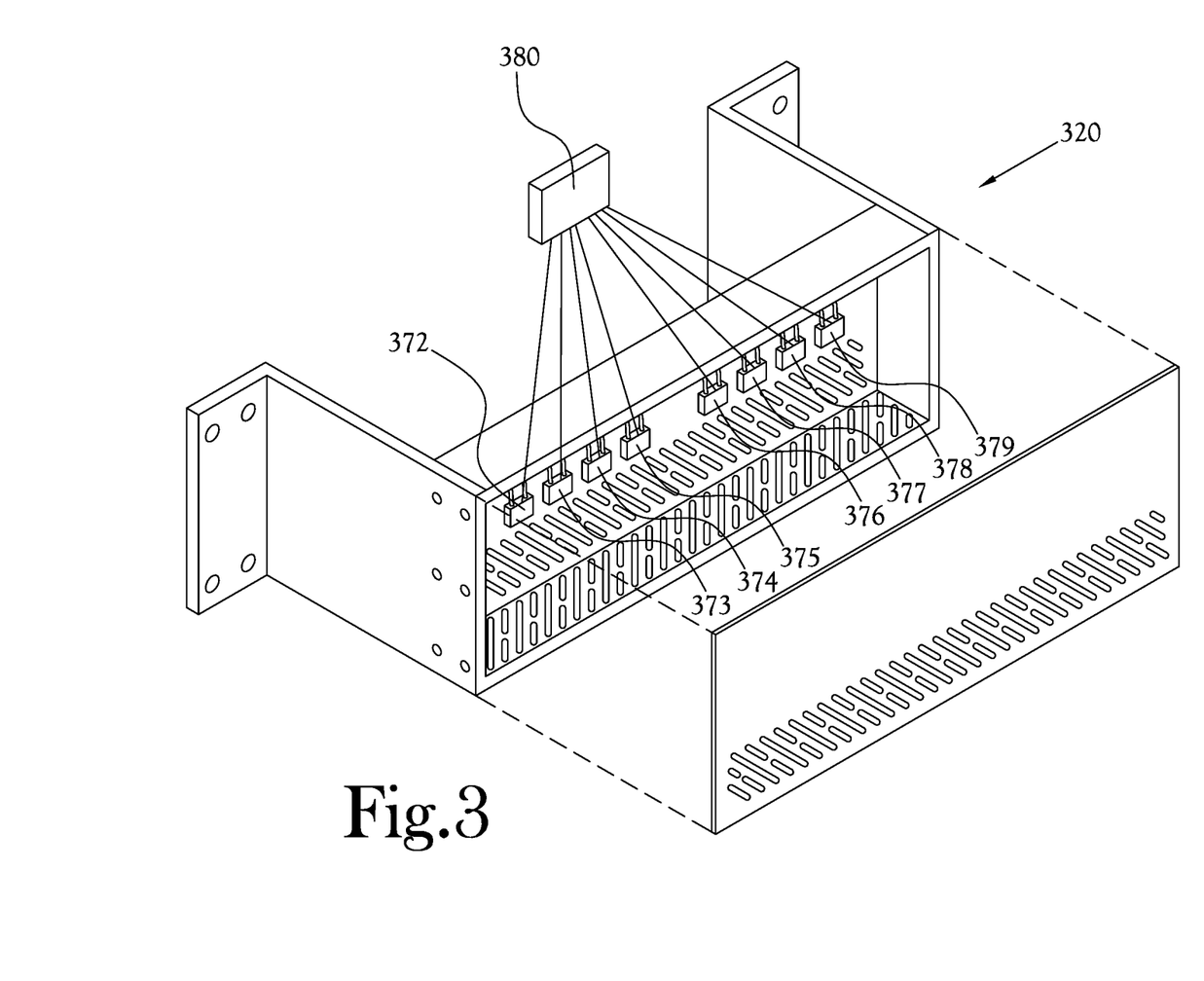
FIG. 3 represents an ozone generator including an enclosure including a back attached to a front through a top, a bottom, a left side, and a right side as previously described with regard to FIG. 2A, FIG. 2B, and FIG. 2C.

FIG. 3 represents an ozone generator 320 including an enclosure including a back attached to a front through a top, a bottom, a left side, and a right side as previously described with regard to FIG. 2A, FIG. 2B, and FIG. 2C. The enclosure also includes attachments that position the ozone generator in a previously existing conditioned airflow as also described with regard to FIG. 2A, FIG. 2B, and FIG. 2C.

The enclosure 320 includes at least eight ozone generation plates 372, 373, 374, 375, 376, 377, 378, and 379. Thus, instead of having at least two pair of ozone generation plates as was the case with the ozone generator 220 from FIG. 2 and FIG. 2A, the ozone generator 320 of FIG. 3 includes at least four pair of ozone generation plates. Thus, each ozone generation plate of the ozone generator 220 of FIG. 2A is replaced with two ozone generation plates in the ozone generator 320 of FIG. 3, allowing for a potential doubling of ozone output for larger enclosed airspaces. The ozone generator 320 may have four independent ozone generation control channels, but with twice the potential ozone output per ozone generation control channel in relation to the ozone generator 220, or if each of the ozone generation plates 372, 373, 374, 375, 376, 377, 378, and 379 are independently operable, eight independent ozone generation control channels may be provided for the ozone generator 320. While not shown in FIG. 3, additional ozone generation plates may be added to one or more of the independent ozone generation control channels to further increase ozone output for larger enclosed airspaces. While a single plate energizer 380 is shown, multiple plate energizers may be used, such as when a separate plate energizer is used for each plate. The ozone generator 320 may include additional components.

Each ozone generation plate may be any device that converts electricity into ozone in the presence of an oxygen-containing atmosphere. The oxygen containing atmosphere may be naturally occurring or enhanced in oxygen content through the use of gaseous oxygen. Preferably, each ozone generation plate can produce at least 600 mg of ozone per hour. More preferable ozone generation plates can produce at least 700 mg of ozone per hour. A presently preferred ozone generation plate is the $A_2Z$ Plate #700, available from $A_2Z$ Ozone, Louisville, Ky.

Figure 4:
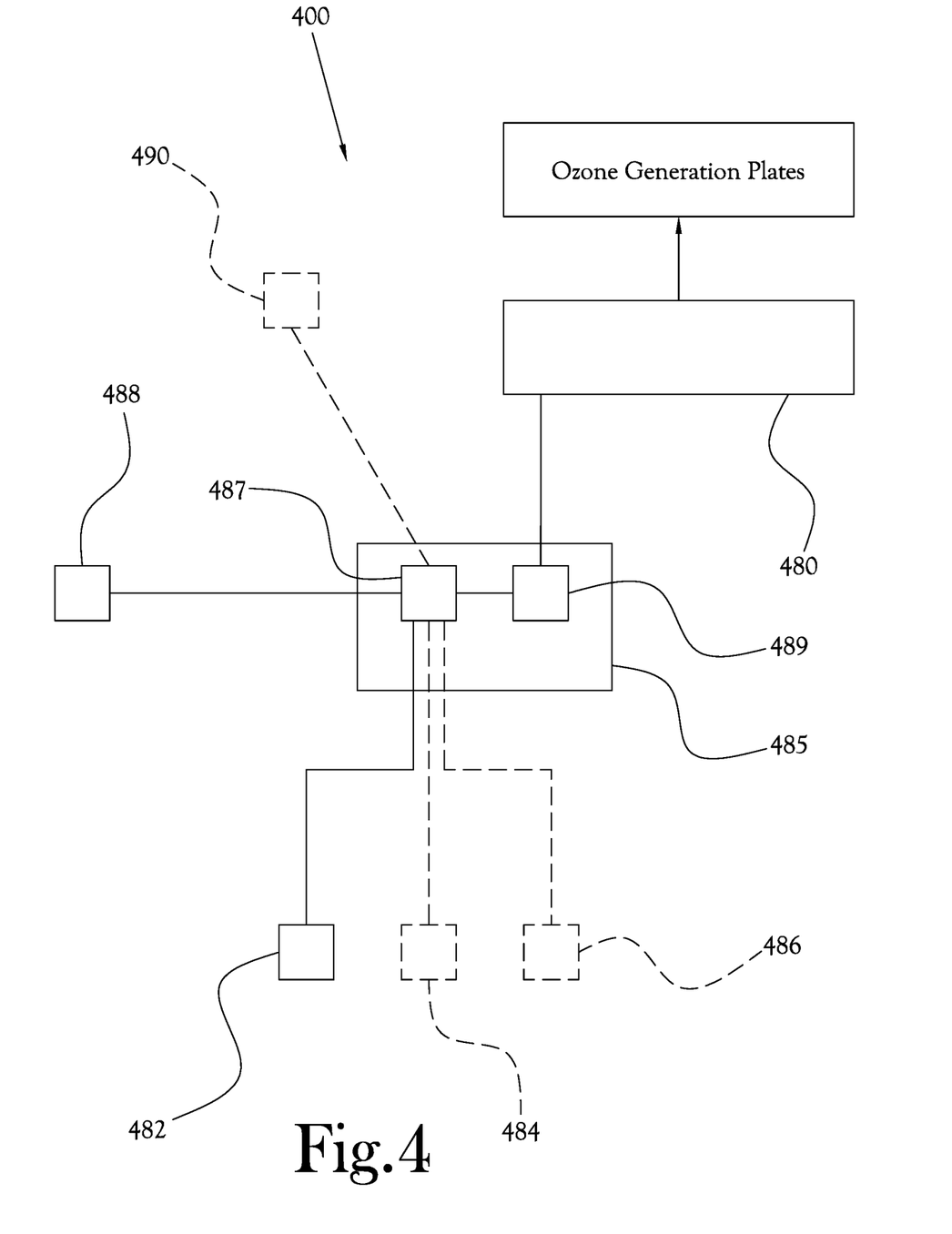
FIG. 4 represents an ozone generation control system including plate energizer, energizer controller, ozone sensor, conditioned air sensor, optional temperature sensor, optional humidity sensor, and optional display controller.

FIG. 4 represents an ozone generation control system 400 including plate energizer 480, energizer controller 485, ozone sensor 482, conditioned air sensor 488, optional temperature sensor 484, optional humidity sensor 486, and optional display controller 490. The optional display controller 490 may provide for user input, such as selection of operation mode, and may display the operation mode and sensor levels associated with the energizer controller 485. The display controller 490 may be analog or digital or both in operation. The display controller 490 may include a LCD, a LED, an OLED, a vacuum fluorescent, or other display adapted to show a numerical reading. Other display types may be used. The display controller 490 electrically communicates with the energizer controller 485. The display controller 490 may be separate from the energizer controller 485, such as when in wireless communication with the energizer controller 485. Alternatively, the display controller 490 may be removed from the energizer controller 485, such as when the energizer controller 485 electrically communicates with a remote computing device, wi-fi network, and the like that electrically communicates with the energizer controller 485.

The ozone sensor 482 determines the ozone content of the air in the conditioned airspace. The ozone content may be measured using an Eco Sensor-OS-6, $A_2Z$ Ozone Sensor-03-100, or Spec Sensor 15×15 20 ppm 110-402, such as available from Eco Sensors, Newark, Calif., $A_2Z$, or SPEC Sensors, Newark Calif., respectively. The ozone sensor 482 may have a measurement range of approximately 0.1 to 4 ppm ozone in the atmosphere. Preferably, the ozone sensor 482 has a measurement range of approximately 0.05 to 20 ppm ozone in the atmosphere. Other sensor types with other operating ranges may be used to determine the ozone content in the air of the conditioned airspace.

The conditioned air sensor 488 determines whether conditioned air is flowing through the ozone generator. The conditioned air sensor 488 may be implemented as an airflow sensor mounted in the ozone generator or elsewhere in the conditioned airflow. Preferably, the conditioned air sensor 488 is implemented as an electrical input from the refrigeration unit that electrically signals when it is operating to condition the air in the enclosed airspace of the container.

The optional temperature sensor 484 determines the temperature of the air in the conditioned airspace. The temperature may be measured using a thermister, thermometer, or other temperature sensing device. Preferably, the temperature sensor 484 has an operational range of approximately −30° C. to 50° C. Other techniques may be used to determine the temperature of the air in the conditioned airspace.

The optional humidity sensor 486 determines the humidity of the air in the conditioned airspace. The humidity may be measured using a Honeywell HIH-5030/5031 series low voltage humidity sensor, such as available from Honeywell, http://sensing.honeywell.com. Other humidity sensors may be used. Preferably, the humidity sensor 486 has a measurement range of approximately 35%-75% relative humidity in the atmosphere. Other techniques and sensors may be used to determine the amount of moisture in the air of the conditioned airspace.

The energizer controller 485 includes processor 487 and storage medium 489. The energizer controller 485 optionally may include a real-time clock with calendar capability (not shown) and other electronics to provide additional features to the energizer controller 485. The storage medium 489 may be a magnetic, optical, or semiconductor memory, another storage device, or the like. The storage medium 489 may be a fixed memory device, a removable memory device, such as a memory card, remotely accessed, or the like. Preferably, the storage medium 489 includes both fixed and removable memory, such as in the form of a SD card or similar removable memory device. In this way, individual trip identity and logging capability along with trip storage capability is provided so the removable memory may be provided to the receiver of the delivered produce and other foods while the delivering carrier also may maintain a permanent record.

The processor 487 determines which of the at least four available independent ozone generation control channels to energize or turn off by supplying the appropriate instruction to the plate energizer or energizers using computer readable non-transient software code and data stored in the storage medium 489. The processor 487 also may store sensor readings, operating times, and status in the storage medium 489 for later review and interpretation by the deliverer and receiver of the produce and other foods. This information also may be transmitted, such as through a wired or wireless network or maintained in the fixed or removable portions of the storage medium 489. In this manner, the deliver and receiver of the transported produce and other foods can have more information regarding the condition of the produce and other foods.

The processor 487 may energize or turn off one or more of the at least four independent ozone generation control channels in response to a reading from the ozone sensor 482, the conditioned air sensor 488, the optional temperature sensor 484, or the optional humidity sensor 486 in any combination. The processor 487 also may energize or turn off one or more of the at least four independent ozone generation control channels in response to user input, such as selection of an available operating mode. The processor 487 may consider the reading from one or more of the sensors and the user selected operating mode to determine which of the at least four independent ozone generation control channels to energize or turn off and for the duration of energized or off operation. The processor 487 also may activate an alarm (not shown) if readings from one or more of the sensors is outside of a predetermined threshold. For example, predetermined alarm thresholds may be stored in the storage medium 489 for upper and lower temperatures and ozone levels. Preferably, the processor 487 does not energize the ozone generation control channels when conditioned air is not flowing through the ozone generator.

Preferably, the computer readable non-transient software code and data stored in the storage medium 489 provides the processor 487 with at least three operating modes. The at least three operating modes include sterilization, disinfecting or produce sterilization, and managing or transport mode. The computer readable non-transient software code and data stored in the storage medium 489 may provide the processor 487 with additional operating modes.

Sterilization mode is implemented by the processor 487 before produce and other foods are loaded into the refrigerated container. Sterilization mode supplies enough ozone to the interior conditioned airspace of the refrigerated container to substantially reduce microorganisms, pesticide residue, odors, and other organic contaminants incompatible with the storage of produce and other foods. Preferably, disinfecting mode kills at least 90% of microorganisms in the enclosed airspace. In sterilization mode, the majority of the available ozone generation control channels are energized. Preferably, all available ozone generation control channels are energized in sterilization mode.

During sterilization mode a concentration from 4 to 8 ppm ozone is generated and maintained in the interior conditioned airspace for a time period from 10 to 20 minutes. Preferably, during sterilization mode a concentration from 4 to 7 ppm ozone is generated and maintained in the interior conditioned airspace for a time period from 12 to 18 minutes. More preferably, during sterilization mode sterilization mode a concentration from 4 to 6 ppm ozone is generated and maintained in the interior conditioned airspace for a time period from 14 to 16 minutes.

Disinfecting mode is implemented by the processor 487 after sterilization mode, but also after produce and other foods are loaded into the refrigerated container. Disinfecting mode may be implemented before or during transport of the produce and other foods. Disinfecting mode supplies enough ozone to the interior conditioned airspace of the refrigerated container to substantially reduce microorganisms, pesticide residue, odors and other organic contaminants incompatible with the storage of produce and other foods introduced to the interior conditioned airspace by the loading of the produce and other foods. Preferably, disinfecting mode kills at least 70% of microorganisms and oxidizes at least 70% of pesticide residue on the produce and other foods. Disinfecting mode also supplies enough ozone to the interior conditioned airspace to oxidize accumulated spoilage gas in the produce and other foods. The generated ozone level in disinfecting mode is less than in sterilization mode to reduce the chance of oxidizing the produce and other foods. In disinfecting mode, half or less of the available ozone generation control channels are energized. Preferably, half of the available ozone generation control channels are energized.

During disinfecting mode, a concentration from 2 to 3.9 ppm, ozone is generated and maintained in the interior conditioned airspace for a time period from 15 minutes to 2 hours, depending on the load of the interior conditioned airspace. Preferably, during disinfecting mode a concentration from 2.5 to 3.9 ppm ozone is generated and maintained in the interior conditioned airspace for a time period from 15 minutes to 1 hour, depending on the load of the interior conditioned airspace. More preferably, during disinfecting mode a concentration from 3 to 3.9 ppm ozone is generated and maintained in the interior conditioned airspace for a time period from 15 to 30 minutes, depending on the load of the interior conditioned airspace.

Managing mode is implemented by the processor 487 after disinfecting mode when produce and other foods loaded into the refrigerated container are disinfected. Managing mode may be implemented before or during transport of the produce and other foods, but preferably during transport. Managing mode supplies enough ozone to the interior conditioned airspace of the refrigerated container to maintain the desired level of spoilage gas and reduce the microorganisms and odors that otherwise would be generated by the produce and other foods during storage and transport. The generated ozone level in managing mode is less than in disinfecting mode to further reduce the chance of oxidizing the produce and other foods during the storage and transport period. In managing mode, one quarter or less of the available ozone generation control channels are energized. Preferably, one quarter of the available ozone generation control channels are energized. If spoilage gas levels increase beyond what managing mode can control, the processor 487 may implement a relatively short duration of disinfecting mode to bring the levels within the desired range.

During managing mode a concentration from 0.5 to 1.5 ppm ozone may be generated and maintained in the interior conditioned airspace for a time period after termination of disinfecting mode and until the produce and other foods are delivered, or a time period less than delivery to allow adequate ozone decomposition before opening of the refrigerated container. For example, the time period less than delivery could be approximately 30 minutes less than delivery. Preferably, during managing mode a concentration from 0.7 to 1.3 ppm ozone is generated and maintained in the interior conditioned airspace for a time period after termination of disinfecting mode and until the produce and other foods are delivered, or a time period less than delivery to allow adequate ozone decomposition before opening of the refrigerated container. More preferably, during managing mode a concentration from 0.9 to 1.1 ppm ozone is generated and maintained in the interior conditioned airspace for a time period after termination of disinfecting mode and until the produce and other foods are delivered, or a time period less than delivery to allow adequate ozone decomposition before opening of the refrigerated container.

In addition to relying on ozone to maintain the desired ozone level for managing mode, during managing mode the ethylene gas level within the interior conditioned airspace may also be monitored. Thus, the level of ozone generated within the interior conditioned airspace may be responsive to ethylene gas levels within the enclosed airspace alone, or in addition to ozone level. If ozone generation is responsive to ethylene gas levels, the conditioned airspace also includes an ethylene gas sensor (not shown) having a measurement range of approximately 0 to 100 ppm in the atmosphere, such as the Honeywell ETO Sensor SR-E04. If so equipped the processor 487 may energize or turn off one or more of the at least four independent ozone generation control channels in response to a reading from the ethylene gas sensor during management mode, as previously discussed with regard to the other sensors.

During managing mode, the processor 487 preferably interleaves energized operation of the at least four ozone generation control channels to prolong the life of the ozone generation plates. Thus, to maintain the ozone level in the interior conditioned airspace as provided by one control channel, the processor 487 can consecutively energize and then turn off each ozone generation control channel for a set time period, such as approximately 15 minutes. In this way, to provide an hour of continuous operation, each of the four available ozone generation control channel is energized for approximately 15 minutes. If more ozone generation control channels are available, the operation of each ozone generation control channel on an hourly basis may further be reduced to prolong the life of the ozone generation plates. Through this interleaved operation, the duty cycle of the individual ozone generation control channels, and thus the ozone generation plates, is reduced. As ozone generation plates have a finite lifespan, the useful life of the ozone generator substantially increases.

In addition to during managing mode, interleaved operation also may be implemented during disinfecting mode as at least four ozone generation control channels are preferably available for interleaving. Thus, of the four available ozone generation control channels, a first two may be energized at the same time during disinfecting mode, which leaves a second two that may be energized at the same time when the first two are turned off. For example, during a one hour disinfecting mode operation, the first two of the four available ozone generation control channels are energized for approximately thirty minutes of the one hour time period, while the second two of the ozone generation control channels would be energized for the remaining approximately thirty minutes of the one hour disinfecting mode operation. While each two of the four ozone generation control channels are energized for approximately thirty minutes of the one-hour time period, the approximately thirty-minute energized period may not be continuous.

To provide a clear and more consistent understanding of the specification and claims of this application, the following definitions are provided.

Bacteria includes, but is not limited to, *Salmonella enteritidis, E. coli* O157:H7, *Listeria monocytogenes, Shigella dysenteriae, Micrococcus aureus, Clostriduim botulinum, Mycobacterium tuberculosis, Bacillus anthracis*, and *Streptococcus* sp.

Mold includes, but is not limited to, *Botrytis, Rhizopus, Penicillium*, and *Aspergillus*.

Spoilage gases, such as ethylene, naturally evolve from produce and other foods. This is nature's way of ripening them. Unfortunately, ethylene along with moisture, also cause decay. Loss of produce and other foods because of premature ripening during storage or transportation can result in the loss of valuable revenue. Ethylene in very small amounts can destroy green leafy vegetables in very short order and can cause significant economic losses for growers, suppliers, markets and florists.

Substantially reduce in the context of microorganism reduction means that at least 70% of the previously living bacteria, viruses, fungus, or mold is killed. Higher kill rates are preferred.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A method of operating a conditioned airflow ozone generator in an enclosed airspace in a previously existing conditioned airflow to extend produce and other foods shelf-life after shipment, the method comprising:

sterilizing an enclosed airspace lacking produce and other foods with a conditioned airflow ozone generator placed in a previously existing conditioned airflow within the enclosed airspace, where the enclosed airspace maintains from 4 to 8 ppm ozone for a time period from 10 to 20 minutes;

placing produce and other foods within the enclosed airspace;

disinfecting the produce and other foods within the enclosed airspace with the conditioned airflow ozone generator placed in the previously existing conditioned airflow, where the enclosed airspace maintains from 2 to 3.9 ppm ozone for a time period from 15 minutes to 2 hours; and managing the produce and other foods within the enclosed airspace with the conditioned airflow ozone generator during transport of the produce and other foods, where the enclosed airspace maintains from 0.5 to 1.5 ppm ozone for a time period after termination of the disinfecting.

2. The method of claim 1, where the sterilizing the enclosed airspace includes operating at least four ozone generation control channels to energize at least four ozone generation plates.

3. The method of claim 2, where each of the at least four ozone generation plates can produce at least 700 milligrams of ozone per hour.

4. The method of claim 1, where the sterilizing the enclosed airspace includes operating at least eight ozone generation control channels to energize at least eight ozone generation plates.

5. The method of claim 1, where during the sterilizing, the enclosed airspace maintains from 4 to 7 ppm ozone for a time period from 12 to 18 minutes.

6. The method of claim 1, where during the sterilizing, the enclosed airspace maintains from 4 to 6 ppm ozone for a time period from 14 to 16 minutes.

7. The method of claim 1, where during the sterilizing, the sterilizing kills at least 90% of microorganisms in the enclosed airspace.

8. The method of claim 1, where the disinfecting the enclosed airspace includes operating at least two ozone generation control channels to energize at least two ozone generation plates.

9. The method of claim 4, where the disinfecting the enclosed airspace includes operating at least four ozone generation control channels to energize at least four ozone generation plates.

10. The method of claim 1, where the disinfecting the produce and other foods includes interleaving at least four ozone generation control channels so that no more than one-half of the available ozone generation plates are simultaneously energized.

11. The method of claim 1, where during the disinfecting, the enclosed airspace maintains from 2.5 to 3.9 ppm ozone for a time period from 15 minutes to 1 hour.

12. The method of claim 1, where during the disinfecting, the enclosed airspace maintains from 3 to 3.9 ppm ozone for a time period from 15 to 30 minutes.

13. The method of claim 1, where during the disinfecting the produce and other foods, the disinfecting kills at least 70% of microorganisms on the produce and other foods.

14. The method of claim 1, where during the disinfecting the produce and other foods, the disinfecting oxidizes at least 70% of pesticide residue on the produce and other foods.

15. The method of claim 1, where the managing the produce and other foods within the enclosed airspace includes using at least one ozone generation control channel to energize at least one ozone generation plate.

16. The method of claim 4, where the managing the produce and other foods within the enclosed airspace includes using at least two ozone generation control channels to energize at least two ozone generation plates.

17. The method of claim 1, where the managing the produce and other foods within the enclosed airspace includes interleaving at least four ozone generation control channels so that no more than one-quarter of the available ozone generation plates are simultaneously energized.

18. The method of claim 1, where the managing the produce and other foods within the enclosed airspace includes interleaving at least eight ozone generation control channels so that no more than one-quarter of the available ozone generation plates are simultaneously energized.

19. The method of claim 1, where during the managing, the enclosed airspace maintains from 0.7 to 1.3 ppm ozone.

20. The method of claim 1, where during the managing, the enclosed airspace maintains from 0.9 to 1.1 ppm ozone.

21. The method of claim 1, further comprising monitoring ozone levels in the enclosed airspace.

22. The method of claim 1, further comprising turning off the conditioned airflow zone generator at a pre-selected time period before the conditioned airspace is entered by a person.

23. The method of claim 1, where the conditioned airspace is a refrigerated container.

24. The method of claim 1, where the conditioned airspace is conditioned by a refrigeration unit.

25. The method of claim 1, where an energizer controller implements the sterilizing, the disinfecting, and the managing in response to a display controller.

26. The method of claim 25, where the display controller provides for user input.

27. The method of claim 25, where the display controller communicates wirelessly with the energizer controller.

28. The method of claim 1, where an energizer controller implements the sterilizing, the disinfecting, and the managing in response to electrical communication with a remote computing device.

29. The method of claim 28, where the electrical communication is through a wi-fi network.

30. The method of claim 1, where the energizer controller includes a processor and a storage medium.

31. The method of claim 25, further comprising remotely accessing the storage medium.

32. The method of claim 30, further comprising logging individual trip identity.

33. The method of claim 30, further comprising storing sensor readings and operating times.

34. The method of claim 30, further comprising transmitting sensor readings and operating times.

35. The method of claim 1, further comprising turning off the conditioned airflow ozone generator after the managing but before delivering the produce and other foods to allow adequate ozone decomposition before opening the enclosed airspace.

36. The method of claim 1, further comprising during the managing monitoring the ethylene gas level within the enclosed airspace and adjusting the ozone level within the enclosed airspace in response to the ethylene gas level.

37. A method of positioning a conditioned airflow ozone generator in a previously existing conditioned airflow, the method comprising:
   determining a region of maximum airflow within an enclosed airspace;
   positioning a conditioned airflow ozone generator so at least a portion of the region of maximum airflow passes through back perforations and front perforations of the conditioned airflow ozone generator; and
   attaching the conditioned airflow ozone generator to an interior wall of the enclosed airspace, where the conditioned airflow ozone generator comprises:
   an enclosure including a back attached to a front through a top, a bottom, a left side, and a right side,
      where from 10% to 70% of the surface area of the back and the front includes perforations allowing passage of a previously existing conditioned airflow,
      where from 30% to 95% of the surface area of the bottom includes perforations allowing passage of the previously existing conditioned airflow,
   at least four independently operable ozone generation plates mounted within the enclosure, where the at least four independently operable ozone generation plates form at least four independent ozone generation control channels, and
   at least one plate energizer in electrical communication with the at least four independently operable ozone generation plates through the at least four independent ozone generation control channels,
      where the at least one plate energizer is in electrical communication with at least one processor and the at least one processor is configured to operate the at least one plate energizer to sterilize an enclosed airspace lacking produce and other foods,
         where the at least one processor is configured to maintain from 4 to 8 ppm ozone for a time period from 10 to 20 minutes in the enclosed airspace lacking produce and other foods during sterilization,
         where the at least one processor is configured after the sterilization to operate the at least one plate energizer to disinfect an enclosed airspace including produce and other foods, where the at least one processor maintains from 2 to 3.9 ppm ozone for a time period from 15 minutes to 2 hours in the enclosed airspace including produce and other foods during disinfecting, and
         where the at least one processor is configured after the disinfecting to operate the at least one plate energizer to manage the produce and other foods within the enclosed airspace including produce and other foods during transport of the produce and other foods, where the at least one processor maintains from 0.5 to 1.5 ppm ozone in the enclosed airspace including produce and other foods during managing the transport of the produce and other foods.

38. The method of claim 37, where the region of maximum airflow within the enclosed airspace originates from a duct and the conditioned airflow ozone generator covers no more than 50% (area/area) of the area of the duct.

39. The method of claim 28, where a portion of the conditioned airflow ozone generator lacking perforations does not cover the area of the duct.

40. The method of claim 37, where the region of maximum airflow within the enclosed airspace originates from a duct and a back of the ozone generator is positioned from 8 to 20 centimeters away from the duct.

41. The method of claim 37, where the back and the front are substantially the same area, the top and the bottom are substantially the same area, and the left and the right sides are substantially the same area.

42. The method of claim 37, where the conditioned airflow ozone generator comprises an enclosure that is rectangular in shape.

43. The method of claim 37, where the at least one processor is configured to manage the ozone level within the enclosed airspace including produce and other foods during the transport of the produce and other foods in response to an ozone sensor and a conditioned air sensor.

44. The method of claim 37, further comprising the at least one processor configured to interleave the at least four independent ozone generation control channels.

45. The method of claim 37, further comprising the at least one processor responsive to a display controller.

46. The method of claim 37, where the conditioned airflow ozone generator further comprises at least eight ozone generation plates mounted within the enclosure.

47. The method of claim 46, where the conditioned airflow ozone generator further comprises at least eight ozone generation control channels.

48. The method of claim 47, where the at least one processor is configured to activate the at least four independent ozone generation control channels during the sterilization.

49. The method of claim 37, where the at least one processor is configured to maintain from 4 to 6 ppm ozone for a time period from 14 to 16 minutes in the enclosed airspace lacking produce and other foods during the sterilization.

50. The method of claim 37, where the at least one processor is configured to kill at least 90% of microorganisms in the enclosed airspace lacking produce and other foods during the sterilization.

51. The method of claim 37, where the at least one processor is configured to activate at least two of the at least four ozone generation control channels during the disinfecting.

52. The method of claim 37, where the at least one processor is configured to activate no more than one-half of the at least four ozone generation control channels simultaneously during the disinfecting.

53. The method of claim 37, where the at least one processor is configured to maintain from 3 to 3.9 ppm ozone for a time period from 15 to 30 minutes in the enclosed airspace including produce and other foods during the disinfecting.

54. The method of claim 37, where the at least one processor is configured to kill at least 70% of microorganisms on the produce and other foods during the disinfecting.

55. The method of claim 37, where the at least one processor is configured to oxidize at least 70% of pesticide residue on the produce and other foods during the disinfecting.

56. The method of claim 37, where the at least one processor is configured to activate no more than one-quarter of the at least four ozone generation control channels simultaneously during the managing.

57. The method of claim 37, where the at least one processor is configured to maintain from 0.9 to 1.1 ppm ozone in the enclosed airspace including produce and other foods during the managing.

* * * * *